(12) United States Patent
Heggie et al.

(10) Patent No.: US 9,072,679 B2
(45) Date of Patent: Jul. 7, 2015

(54) PARTICLES OF TETRACYCLINES AND PROTECTING AGENT

(75) Inventors: William Heggie, Palmela (PT); Cristina Maria Sanches Simoes de Faria, Lisbon (PT)

(73) Assignee: HOVIONE INTER LIMITED, Lucerne (CH)

( * ) Notice: Subject to any disclaimer, the term of this patent is extended or adjusted under 35 U.S.C. 154(b) by 107 days.

(21) Appl. No.: 13/697,897

(22) PCT Filed: May 12, 2011

(86) PCT No.: PCT/GB2011/000729
§ 371 (c)(1),
(2), (4) Date: Feb. 11, 2013

(87) PCT Pub. No.: WO2011/141708
PCT Pub. Date: Nov. 17, 2011

(65) Prior Publication Data
US 2013/0195986 A1    Aug. 1, 2013

(30) Foreign Application Priority Data
May 14, 2010  (PT) .................... 105116

(51) Int. Cl.
| | |
|---|---|
| A61K 9/50 | (2006.01) |
| A61K 9/127 | (2006.01) |
| A61K 9/20 | (2006.01) |
| A61K 9/51 | (2006.01) |
| A61K 9/16 | (2006.01) |
| A61K 31/375 | (2006.01) |
| A61K 31/65 | (2006.01) |
| A61K 45/06 | (2006.01) |
| A61K 47/22 | (2006.01) |

(52) U.S. Cl.
CPC ............. *A61K 9/5042* (2013.01); *A61K 9/127* (2013.01); *A61K 9/1271* (2013.01); *A61K 9/205* (2013.01); *A61K 9/5161* (2013.01); *A61K 9/1647* (2013.01); *A61K 9/1617* (2013.01); *A61K 9/1652* (2013.01); *A61K 31/375* (2013.01); *A61K 31/65* (2013.01); *A61K 45/06* (2013.01); *A61K 9/5089* (2013.01); *A61K 47/22* (2013.01)

(58) Field of Classification Search
CPC ....... A61K 9/127; A61K 9/1271; A61K 8/14; A61K 9/1652; A61K 9/205; A61K 9/5861; A61K 9/5161; A61K 9/1647
See application file for complete search history.

(56) References Cited

U.S. PATENT DOCUMENTS

| | | |
|---|---|---|
| 2004/0121003 A1 | 6/2004 | Chickering, III et al. |
| 2005/0019396 A1 | 1/2005 | deVries et al. |
| 2006/0183719 A1 | 8/2006 | deVries et al. |

FOREIGN PATENT DOCUMENTS

| | | |
|---|---|---|
| GB | 785574 | 10/1957 |
| GB | 895027 | 4/1962 |

OTHER PUBLICATIONS

Bowles, William H., "Protection against Minocycline Pigment Formation by Ascorbic Acid (Vitamin C)", Journal of Esthetic Dentistry, 1998, vol. 10, No. 4, pp. 182-186.
Cheek et al., "Dental and oral discolorations associated with minocycline and other tetracycline analogs", Journal of Esthetic Dentistry, 1999, vol. 11, No. 1, pp. 43-48.
PCT International Preliminary Report on Patentability, Application PCT/GB2011/000729, dated Aug. 31, 2012.
PCT International Search Report and Written Opinion, Application PCT/GB20111000729, dated Dec. 2, 2011.

*Primary Examiner* — Carlos Azpuru
(74) *Attorney, Agent, or Firm* — MacMillan, Sobanski & Todd, LLC

(57) ABSTRACT

Particles containing a tetracycline or one of its pharmaceutically acceptable salts and an antioxidant, formulations containing the same and their use in the treatment of infectious diseases are described. Methods of encapsulation of a tetracycline or one of its pharmaceutically acceptable salts and an antioxidant are also disclosed.

14 Claims, 2 Drawing Sheets

PARTICLES OF TETRACYCLINES AND PROTECTING AGENT

CROSS-REFERENCE TO RELATED APPLICATIONS

The present invention claims the benefit of the PCT/GB2011/000729 filed May 12, 2011, which claims priority to Ser. PT/105116 filed May 14, 2010.

BACKGROUND OF THE INVENTION

Tetracyclines are broad-spectrum antibiotics, indicated for use against many bacterial infections. Although widely utilized their use has been associated with intrinsic staining of human teeth (especially in children), bones, and soft tissues. This staining has been recognized as being due to an oxidation reaction.

Laboratory studies have shown that the pigment formation can be induced by exposure to ultraviolet light in the presence of air. Animal studies, in rats, have established that simultaneous administration of ascorbic acid (vitamin C) with minocycline prevented staining of the teeth and bones and pigmentation of the thyroid gland (see "Bowles W H, Protection against minocycline pigment formation by ascorbic acid (vitamin C), J. Esthet. Dent. 1998; 10(4): 182-6").

In order to solve the problem of tetracycline induced staining of human teeth, bones and soft tissues; we have now developed a concept for co-administration of a tetracycline and an antioxidant by means of combining, in a particle, the tetracycline or one of its pharmaceutically acceptable salts and an antioxidant. The proportions of the tetracycline and antioxidant can be varied over a wide range and are not limited by any particular physical or chemical constraint. For example, it is envisaged that the particle may comprise from 90% w/w tetracycline/10% w/w antioxidant to 10% w/w tetracycline/90% w/w antioxidant.

SUMMARY OF THE INVENTION

In a broad aspect, the present invention provides a particle comprising a tetracycline and an antioxidant characterized in that the tetracycline and the antioxidant are encapsulated in a polymeric material. Preferably, the particle is a spray dried particle.

In another aspect, the invention provides a method of producing a particle comprising a tetracycline and an antioxidant characterized in that the method comprises the step of encapsulation of the tetracycline and the antioxidant. Preferably, the tetracycline and the antioxidant are encapsulated in a polymeric material.

In another aspect, the invention provides a pharmaceutical formulation characterized in that it comprises one or more particles according to the invention and, where necessary, one or more pharmaceutically acceptable excipients.

The invention also provides a pharmaceutical formulation according to the invention for use as a medicament, for example for use in the treatment of infectious diseases.

The invention also provides a method of co-administration of a tetracycline and an anti-oxidant characterized in that it comprises the administration of a pharmaceutical composition comprising a tetracycline and an antioxidant encapsulated in a polymeric material.

Also provided by the invention is a method of avoiding staining of human teeth, bones, and soft tissues provoked by a tetracycline characterized in that it comprises the administration of a pharmaceutical composition comprising a tetracycline and an antioxidant encapsulated in a polymeric material. Although the effects of said method may be considered as cosmetic the method is essentially preventive in nature.

The invention thus also provides the use of an antioxidant to prevent staining of human teeth, bones, and soft tissues provoked by a tetracycline. This use or method results in a cosmetic effect by preventing staining of human teeth, bones, and soft tissues provoked by a tetracycline. The antioxidant may, for example, be used in a pharmaceutical composition comprising the tetracycline, such as a composition of the invention.

DETAILED DESCRIPTION OF THE INVENTION

Figure 1A:
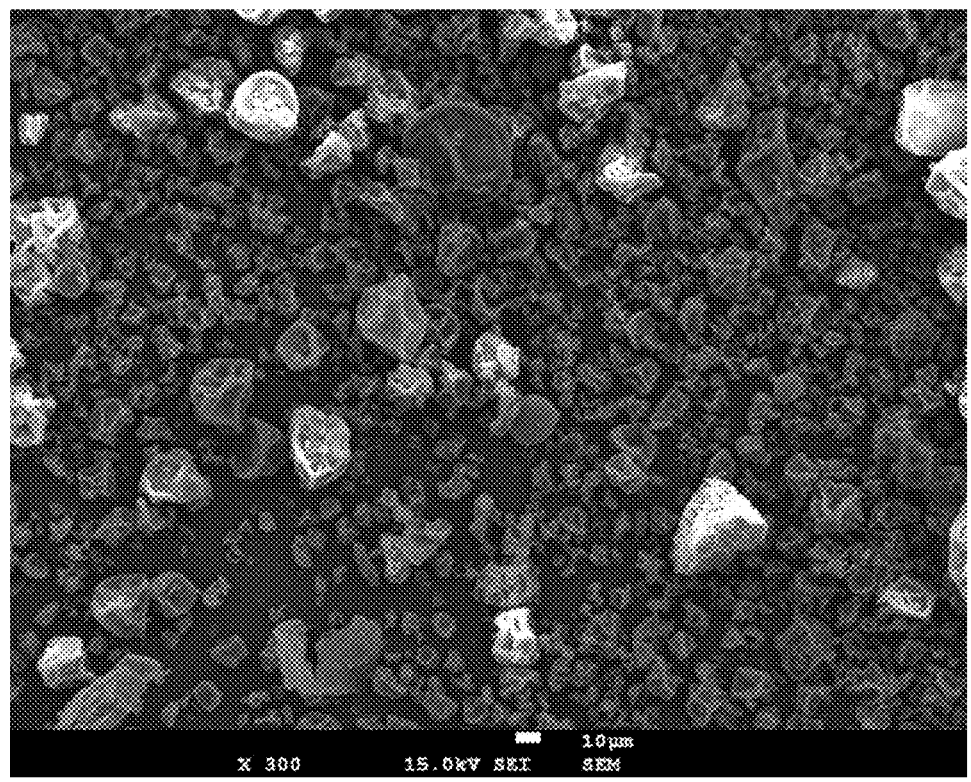
FIGS. 1a-1d: Scanning electron microscopy photographs showing particles that are collapsed spheres and that the crystals of active materials are contained therein.

In the context of the present invention, "encapsulation" refers to the coating of particles with another material. It is well known to those knowledgeable in the art that the efficiency of the encapsulation process is variable and that the coating material in some particles may not cover the total outer surface of the material in the interior of the particle. Hence particles with this reduced covering by the coating material are also considered to form part of this invention.

Suitable mixing techniques can be applied to obtain an intimate mixture of the components. These mixing techniques are well known in the pharmaceutical industry. At the same time, if so desired, the particle size of the components can be adjusted using well known particle size reduction techniques, examples being milling and wet milling, especially high pressure homogeneous mixing. In a preferred aspect of this invention the micro particles are made by encapsulation of the components in a suitable polymer or other material.

Processes for the encapsulation of tetracyclines forming particles are known e.g US 2004/0121003.

Encapsulation agents can be chosen from any of those known from the literature, such as: Polysaccharides (e.g. starches, maltodextrines and gum arabic), Lipids (e.g. stearic acid, mono and diglycerides, among others) Proteins (e.g. gelatins, casein, soy), Polymers (e.g. hydroxypropylmethyl cellulose and its derivatives (e.g. hydroxypropylmethyl cellulose acetate succinate (HPMCAS), polymethacrylate and its derivatives, polyvinylpirrolidone and its derivatives, poliethyleneglycol and its derivatives).

Melt extrusion procedures may also be applied to obtain mixing and encapsulation.

The particles, wherein the tetracycline and the antioxidant are encapsulated, not only offers improved stability of the tetracycline by protection from atmospheric moisture and oxygen but delivers both components simultaneously in precise and fixed proportions.

The tetracycline can be chosen from any of the compounds belonging to this class that show antibacterial activity or one of its pharmaceutically acceptable salts.

Preferably the tetracycline is minocycline, doxycycline, tigecycline, tetracycline or one of their pharmaceutically acceptable salts. Particularly preferred compounds for use in the invention include doxycycline hyclate and minocycline hydrochloride.

The antioxidant can be chosen from any of the compounds having antioxidant activity such as ascorbic acid (vitamin C);

Tocopherols and Tocotrienols (e.g. vitamin E); Carotenes; Flavonoids (e.g. quercetin) or mixtures thereof.

Preferably the antioxidant is ascorbic acid (vitamin C) or quercetin.

In a preferred embodiment of this invention the particles comprise either doxycycline or minocycline as the hydrochloride or base and ascorbic acid (vitamin C) or quercetin. In addition a preferred polymer is hydropropylmethyl cellulose acetate succinate (HPMCAS).

The particles may contain the tetracycline and the antioxidant in any variable molar proportions depending on the desired ratio.

The particles can be produced by known physical methods (e.g. pan-coating, air-suspension coating, centrifugal or melt extrusion, vibrational nozzle or spray-drying) or chemical methods (e.g. interfacial polymerization, in-situ polymerization, matrix polymerization) or any other known method as referred to in the literature, as will be clear to those skilled in the art.

In a preferred embodiment of this invention the particles are made by spray drying.

The particles can be formulated with any adequate pharmaceutically acceptable excipient for oral, parenteral, topical, periodontal, pulmonary, vaginal or ophthalmic delivery.

The formulated particles can be used in the treatment of any infectious disease responsive to treatment with a tetracycline, namely mucosae or skin infections such as acne or rosacea, but other infections are also treatable using this new and novel formulation, namely infections of the mouth, the ear and respiratory or urinary tracts.

In a preferred embodiment of the invention the tetracycline and the antioxidant are suspended in a non-solvent, to produce a homogeneous mixture and the suspension spray dried. Dichloromethane and acetone or mixtures are preferred but other volatile solvents can be used. The resulting encapsulated material can be post dried if necessary to reduce the levels of the solvent.

Suitable spray drying equipment is available commercially to carry out the spray drying. A preferred nozzle is a two fluid nozzle with a cap and diameter of 1.4 and 0.7 mm respectively, although different types of nozzles and differing dimensions can be used to obtain good results.

EXAMPLES

The following examples are illustrative and in no way restrict the scope of the invention.

TABLE 1

| | Notation | |
|---|---|---|
| PSD | Particle size distribution | |
| PS | Particle size | |
| C_feed | Feed concentration | Solids content in the feed |
| F_feed | Feed flow | Feed Flow rate in the spray dryer step |
| T_in | Inlet temperature | Drying gas temperature at the inlet of the drying chamber |
| T_out | Outlet temperature | Drying gas temperature at the outlet of the drying chamber |
| R_atomiz | Atomization ratio | F_atomiz/F_feed (two fluid nozzle) |

Solution/Suspension Preparation

The suspensions were prepared as follows:
Charge the required amount of DCM/Acetone (75/25% w/w) in a flask;
Add the required amount of polymer HPMCAS under stirring;
Stir until complete dissolution;
Suspend in the above flask the required quantity of antioxidant (Sodium Ascorbate or Quercetin) under stirring; and
Suspend in the above flask the required amount of API (Minocycline HCl or Doxycycline Hyclate)

TABLE 2

| Materials | | Ex a | Ex b | Ex c | Ex d |
|---|---|---|---|---|---|
| Doxycycline hyclate | g | 3.0 | 3.5 | — | — |
| Minocycline hydrochloride | g | — | — | 3.5 | 3.5 |
| Sodium Ascorbate | g | 3.0 | — | — | 3.5 |
| Quercetine | g | — | 3.5 | 3.5 | — |
| HPMCAS | g | 6.0 | 7.0 | 7.0 | 7.0 |
| TOTAL SOLIDS | g | 12.0 | 14.0 | 14.0 | 14.0 |
| Acetone | g | 27.0 | 31.5 | 31.5 | 31.5 |
| Dichloromethane | g | 81.0 | 94.5 | 94.5 | 94.5 |
| TOTAL SOLVENTS | g | 108.0 | 126.0 | 126.0 | 126.0 |
| C_feed | % w/w | 10.0 | 10.0 | 10.0 | 10.0 |
| Composition of the solid (% w/w) | | | | | |
| Doxycycline hyclate | | 25 | 25 | — | — |
| Minocycline hydrochloride | | — | — | 25 | 25 |
| Sodium Ascorbate | | 25 | — | — | 25 |
| Quercetine | | — | 25 | 25 | — |
| HPMCAS | | 50 | 50 | 50 | 50 |
| Composition of the solvent (% w/w) | | | | | |
| Acetone | | 25 | 25 | 25 | 25 |
| Dichloromethane | | 75 | 75 | 75 | 75 |

Spray Drying

A laboratory scale spray dryer was used in these trials. The unit was equipped with a two fluid nozzle, where nozzle cap and diameter were 1.4 and 0.7 mm, respectively. A high-performance cyclone was used to collect the dried product.

The spray drying unit was operated with nitrogen and in single pass mode, i.e. without recirculation of the drying nitrogen. The aspirator, blowing nitrogen, was set at 100% of its capacity (flow rate at maximum capacity is approximately 40 kg/h). The flow rate of the atomization nitrogen was about 0.32 kg/h (corresponding to 20 mm in the rotameter of the equipment).

Before feeding the stock solution/suspension, the spray dryer was stabilized with solvent (water). During the stabilization period, the solvent flow rate was adjusted in order to give the target outlet temperature (the inlet temperature of the drying gas was imposed through the heater set-point). After stabilization of the outlet temperature, the feed of the spray dryer was commuted from the solvent to the product solution (flow rate was then readjusted to maintain the outlet temperature in the target value). At the end of the stock solution/suspension, the feed was once more commuted to solvent, in order to rinse the feed line and to carry out a controlled shut down of the unit.

Yield was calculated as the mass percentage of the dry product collected under the first cyclone in relation to the total solids in the solution/suspension fed to the spray dryer.

TABLE 3

| Parameters | | | | | |
|---|---|---|---|---|---|
| Spray drying parameters | | Ex a | Ex b | Ex c | Ex d |
| T_in | ° C. | 47 ± 1 | 45 ± 1 | 44 ± 1 | 48 ± 1 |
| T_out | ° C. | 40 ± 1 | 39 ± 1 | 37 ± 1 | 41 ± 1 |

TABLE 3-continued

| Parameters | | | | | |
|---|---|---|---|---|---|
| Spray drying parameters | | Ex a | Ex b | Ex c | Ex d |
| F_atomiz | kg/h | 0.32 | 0.32 | 0.32 | 0.32 |
| F_feed | kg/h | 0.30 | 0.30 | 0.30 | 0.30 |
| R_atomiz | — | 1.1 | 1.1 | 1.1 | 1.1 |

Results

Figure 1B:
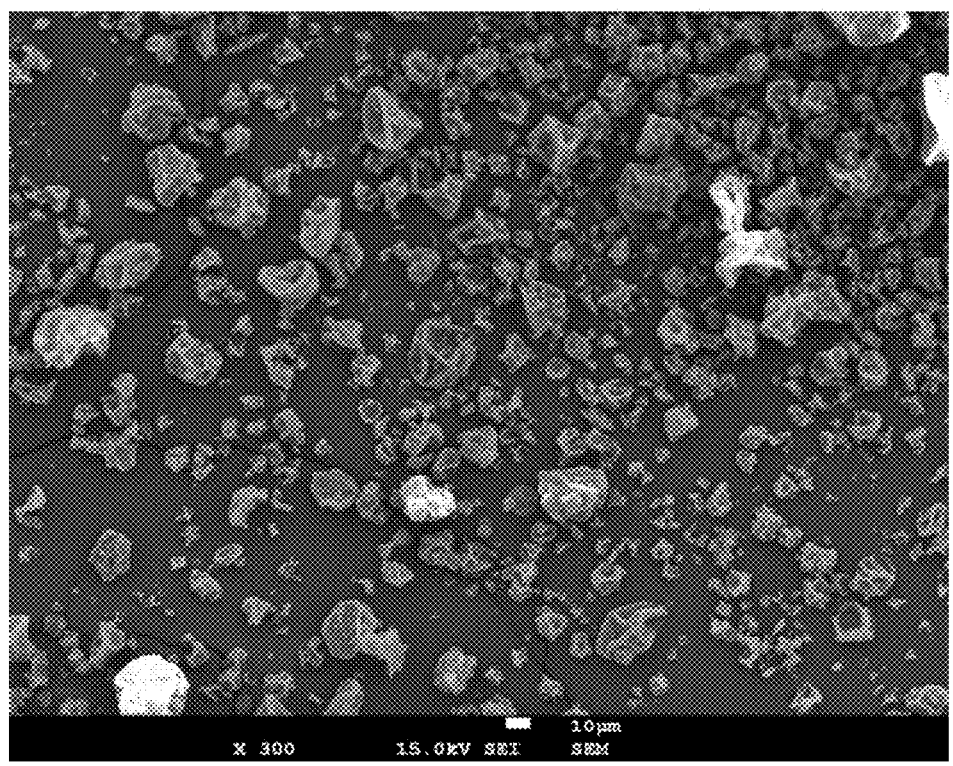
Figure 1C:
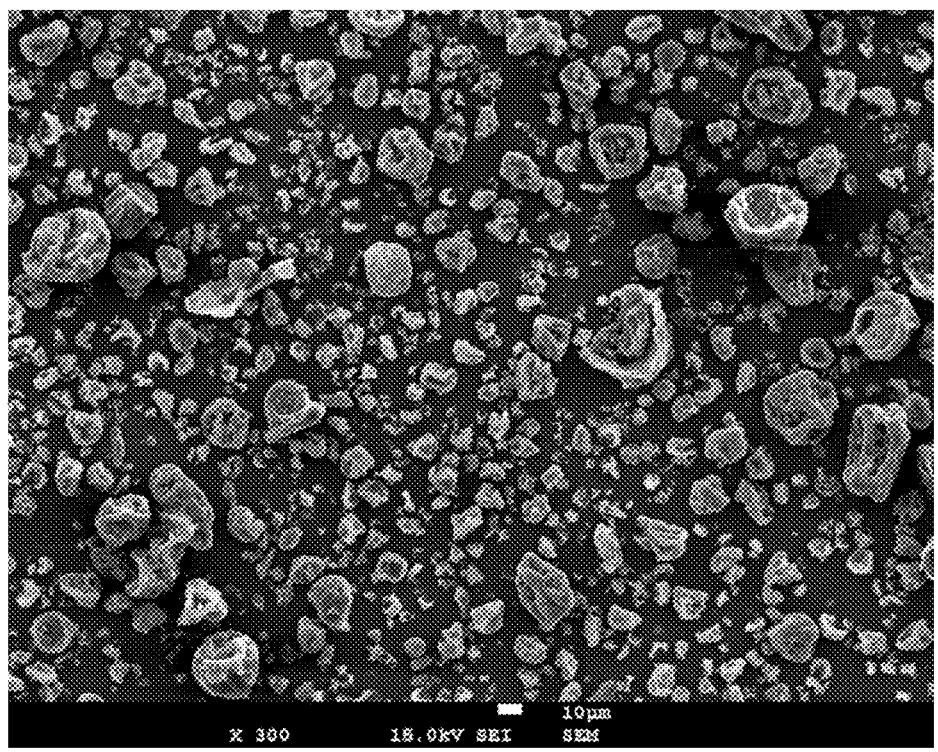
Figure 1D:
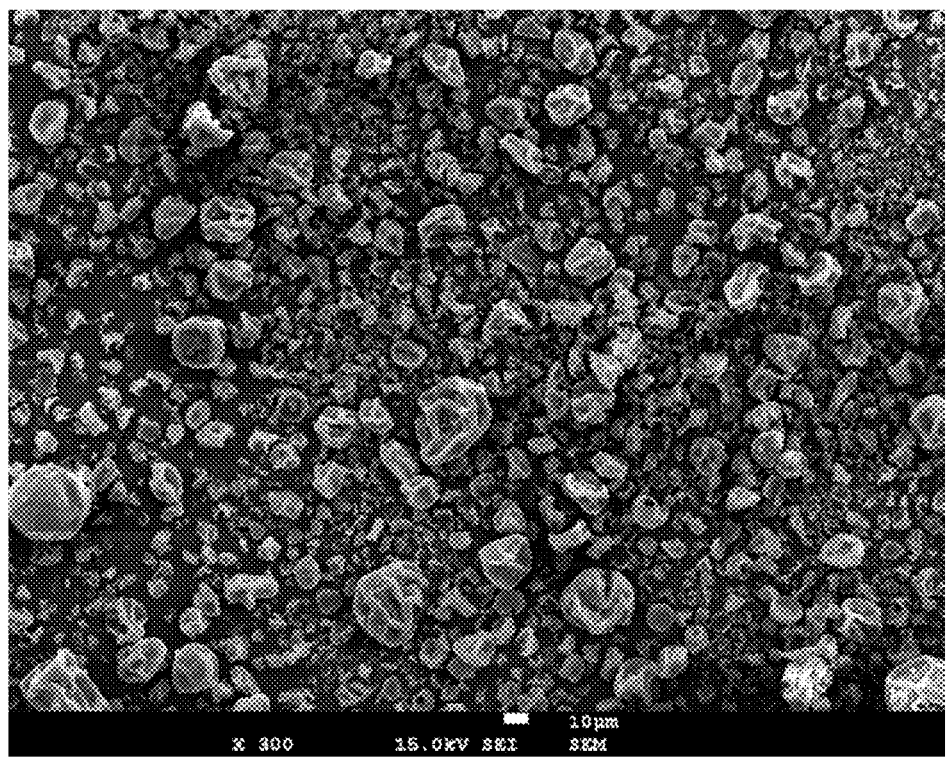

The microencapsulated material powder was analyzed for impurity profile of the tetracycline by HPLC (see Tables 4 and 5) and morphology by scanning electron microscopy (see FIG. 1). The figure shows that the particles are collapsed spheres and that the crystals of active materials are contained therein.

TABLE 4

| Results | | |
|---|---|---|
| | Ex a | Ex b |
| Related substances (6-Epidoxycycline) | 0.13% | 0.09% |
| Related substances (Methacycline) | 0.019% | 0.013% |
| Other impurities | 0.00% | 0.00% |
| Related substances Total impurities | 0.46% | 0.18% |

TABLE 5

| Results | | |
|---|---|---|
| | Ex c | Ex d |
| Related substances (7-monodemethylminocycline) | 0.12% | 0.11% |
| Related substances (5a,6-anhydro minocycline) | 0.20% | 0.20% |
| Related substances (4-Epiminocycline) | 0.78% | 1.31% |
| Related substances NHM, N2-(methylhydroxy)-minocycline | 0.14% | 0.14% |
| Total impurities | 2.1% | 2.6% |

The invention claimed is:

1. A particle comprising a tetracycline and an antioxidant characterized in that the tetracycline and the antioxidant are encapsulated in a polymeric material,
wherein the particle comprises from 90% w/w tetracycline/10% w/w antioxidant to 10% w/w tetracycline/90% w/w antioxidant.

2. A particle according to claim 1 characterized in that the tetracycline is doxycycline, minocycline, tigecycline or tetracycline or one of their pharmaceutically acceptable salts.

3. A particle according to claim 1 wherein the tetracycline is doxycycline or minocycline or a pharmaceutically acceptable salt thereof.

4. A particle according to claim 1, characterized in that the antioxidant is ascorbic acid (vitamin C); a tocopherol or a tocotrienol; a carotene; a flavonoid or a mixture of one or more of the above.

5. A particle according to claim 1, wherein the antioxidant is ascorbic acid (vitamin C) or quercetin.

6. A particle according to claim 1, characterized in that the particle comprises one or more of: a polysaccharide, a lipid, a protein, a polymer; or a mixture of one or more of the above.

7. A particle according to claim 6 wherein the polymer is a hydropropylmethyl cellulose derivative.

8. A particle according to claim 1, characterised in that the particle is a spray dried particle.

9. A particle according to claim 1, characterized in that the antioxidant comprises one or more of vitamin E and quercetin.

10. A particle according to claim 6, characterized in that the polysaccharide comprises one or more of a starch, a maltodextrine, or gum Arabic; the lipid comprises one or more of stearic acid or a mono or diglyceride; the protein comprises one or more of gelatin, casein, or soy; the polymer comprises one or more of hydroxypropylmethyl cellulose or its derivatives, polymethacrylate or its derivatives, polyvinylpyrrolidone or its derivatives, polyethyleneglycol or its derivatives; or, a mixture of one or more of the above.

11. A particle according to claim 7, characterized in that the hydropropylmethyl cellulose derivative comprises hydropropylmethyl cellulose acetate succinate.

12. A particle according to claim 1, characterized in that the tetracycline is protected from atmospheric moisture and oxygen.

13. A particle according to claim 1, characterized in that the tetracycline and antioxidant are isolated from other excipients in the particle.

14. A particle according to claim 1, comprising a tetracycline and an antioxidant characterized in that the tetracycline and the antioxidant are encapsulated in a polymeric material, wherein the particle comprises a hydropropylmethyl cellulose derivative comprising hydropropylmethyl cellulose acetate succinate.

* * * * *